US00PP15960P3

(12) United States Plant Patent
Meilland

(10) Patent No.: US PP15,960 P3
(45) Date of Patent: Sep. 13, 2005

(54) SHRUB ROSE PLANT NAMED 'MEIGLISE'

(50) Latin Name: *Rosa hybrida*
Varietal Denomination: Meiglise

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 152 days.

(21) Appl. No.: 10/740,898

(22) Filed: Dec. 22, 2003

(65) Prior Publication Data

US 2005/0138699 P1 Jun. 23, 2005

(51) Int. Cl.[7] ..... A01H 5/00

(52) U.S. Cl. ..... Plt./103

(58) Field of Search ..... Plt./103, 110, 116, Plt./124

*Primary Examiner*—Howard J. Locker
(74) *Attorney, Agent, or Firm*—Burns, Doane, Swecker & Mathis, LLP

(57) ABSTRACT

A new and distinct variety of Shrub rose plant is provided which forms in clusters attractive single fragrant bright white blossoms. The blossom coloration is well maintained upon maturity and the blossoms self clean well. The plant exhibits a spreading ground cover growth habit. Excellent resistance to Black Spot, Powdery Mildew and Rust is displayed. The very glossy medium green foliage contrasts nicely with the white blossom coloration. The new variety is particularly well suited for providing attractive ornamentation as a mass planting.

5 Drawing Sheets

Botanical/commercial classification: *Rosa hybrida*/Mini Ground Cover Shrub Rose Plant.
Varietal denomination: cv. 'Meiglise'.

SUMMARY OF THE INVENTION

The new variety of Shrub rose plant was created by artificial pollination wherein two parents were crossed which previously had been studied in the hope that they would contribute the desired characteristics. The female parent (i.e., the seed parent) was the product of the cross of *Rosa wichuriana* (non-patented in the United States) and 'The Fairy' variety (non-patented in the United States). The male parent (i.e., the pollen parent) was the 'Korbin' variety (non-patented in the United States). The 'Korbin' variety is marketed under the ICEBERG trademark. The parentage of the new variety can be summarized as follows:

(*Rosa wichuriana*×'The Fairy')×'Korbin'.

The seeds resulting from the above pollination were sown and small plants were obtained which were physically and biologically different from each other. Selective study resulted in the identification of a single plant of the new variety.

It was found that the new Shrub rose variety of the present invention (a) exhibits a spreading ground cover growth habit, (b) abundantly forms in clusters on a nearly continuous basis attractive single fragrant bright white blossoms that self clean well, (c) forms very glossy medium green foliage that contrasts well with the blossom coloration, (d) develops well following the rooting of cuttings, budding and grafting, (e) is highly resistant to Black Spot, Powdery Mildew and Rust, and (f) is particularly well suited for providing attractive ornamentation as a mass planting.

The new variety well meets the needs of the horticultural industry and can be grown to advantage in parks and gardens where attractive ornamentation is desired. It is particularly well suited for growing in small areas as a ground cover and in mass plantings.

The new variety can be readily distinguished from its ancestors. For instance, *Rosa wichuriana* is considerably more spreading and can reach widths of 6 or more meters. 'The Fairy' variety forms double light pink blossoms, and the 'Korbin' variety forms dissimilar larger double white blossoms.

The new variety has been found to undergo asexual propagation at West Grove, Pa., U.S.A., and at Wasco, Calif., U.S.A., by a number of routes, including budding, grafting, and by the use of cuttings. Asexual propagation by the above-mentioned techniques at Pennsylvania and California, has shown that the characteristics of the new variety are stable and are strictly transmissible by such asexual propagation from one generation to another. Good plant development is displayed regardless of the mode of asexual propagation.

The new variety has been named the 'Meiglise' variety, and is being marketed under the WHITE DRIFT trademark.

BRIEF DESCRIPTION OF THE PHOTOGRAPHS

The accompanying photographs show as nearly true as it is reasonably possible to make the same, in a color illustrations of this character, typical specimens of the new variety. The rose plants of the new variety were approximately three years of age and were photographed during October 2003 while growing outdoors on 'Dr. Huey' rootstock in containers at West Grove, Pa., U.S.A. Dimensions in centimeters are included at the bottom of each photograph.

DETAILED DESCRIPTION

The chart used in the identification of the colors is that of The Royal Horticultural Society (R.H.S. Colour Chart). The description is based on the observation of three-year-old plants during October 2003 while growing outdoors on 'Dr. Huey' rootstock in containers at West Grove, Pa., U.S.A.

Class: Shrub.

Plant:

*Height.*—Approximately 25 to 40 cm on average at the end of the growing season.

*Width.*—Approximately 1 to 1.5 m on average at the end of the growing season.

*Habit.*—Forms a low-spreading mound.

Figure 5:
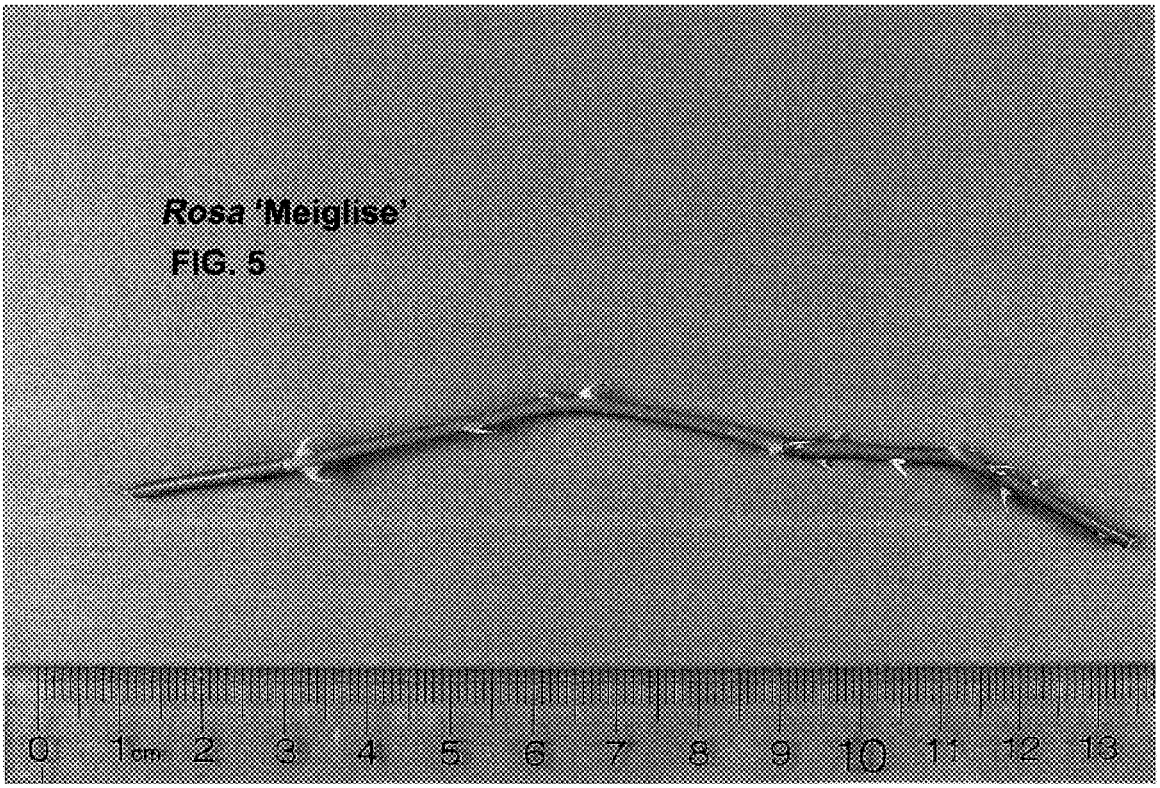
FIG. 5 illustrates a specimen of typical stem with prickles following the removal of leaves.

Branches:

*Thorns.*—Size: Relatively small as illustrated in FIG. 5. Quantity: Typically approximately 8 to 15 on a stem having a length of 10 cm. Configuration: Commonly sharply hooked with the terminal portion commonly nearly parallel to the stem and pointing downward. Color: Near Green Group 138A on young stems, and near Green Group 137A on mature wood and more glaucous.

Leaves:

*General appearance.*—Small, dense, medium green, and glossy.

*Size.*—Varies widely within and between leaflet numbers. Mature 5-leaflet leaves typically are approximately 4 to 5 cm in length, and approximately 3 to 3.5 cm in width. Mature 7-leaflet leaves typically are approximately 5 to 6 cm in length, and approximately 2.6 to 3.3 cm in width. Mature 9-leaflet leaves typically are approximately 5.5 to 8 cm in length, and approximately 3 to 4 cm in width.

*Leaflets.*—Number: Rarely 3, more commonly 5, more typically 7, and rarely 9. Arrangement: Alternate and odd pinnately compound. Shape: Typically elliptical to broadly elliptical to obovate to occasionally broadly obovate. Apex: Typically broadly acute to rounded to nearly truncate. Base: Typically broadly rounded to cuneate to occasionally oblique. Margin: Serrulate. Texture: Glabrous on the upper and under surfaces and papyraceus. Color (adult foliage): Upper surface: Near Green Group 139A. Under surface: Near Green Group 138A with some darkening near Green Group 137C.

Inflorescence:

*Number of flowers.*—Typically approximately 1 to 8 per stem, and more commonly 4 to 5 per stem.

*Bearing.*—In clusters.

*Peduncle.*—Commonly approximately 13 to 20 mm in length and approximately 0.9 to 1 mm in diameter.

*Sepals.*—Number: 5. Extensions: Few in number and foliaceous. Shape: Typically lanceolate. Size: Typically approximately 7 to 11 mm in length, and approximately 2.5 to 4.5 mm in width. Color: Commonly near Green Group 143A on the inner and outer surfaces.

*Buds.*—Ovoid and very small.

*Flower.*—Shape: Single and relatively flat when fully open. Diameter: Approximately 2 to 4.5 cm on average when fully open. Color (open blossom): Upper surface: White Group 155D. Lower surface: White Group 155D. Color stability: Very good with the coloration commonly being well maintained to full maturity. Fragrance: Relatively strong. Petal number: Commonly 6 per blossom under normal growing conditions. Petal shape: Obovate to narrowly obovate to narrowly obcordate. Petaloids: None observed. Petal texture: Glabrous, membranaceus, relatively thin and semi-translucent. Petal margin: Entire though tends to be revolute to a slight degree. Petal apex: Distinctly emarginated. Petal base: Narrowly rounded to rounded to cuneate to narrowly cuneate. Petal size: Typically approximately 1.5 to 2 cm in length and approximately 0.9 to 1.4 cm in width. Petal drop: Very good with the petals detaching cleanly before drying. Pollen: Present and yellow in coloration. Receptacle: Slightly glaucous, commonly approximately 2.5 to 2.8 mm in size when the flower is fully open, and near Green Group 138A in coloration. Hips: Rarely observed.

Development:

*Vegetation.*—Vigorous procumbent thin branches with upright thin shoots and a generally restrained growth.

*Blooming.*—Abundant and nearly continuous.

*Resistance to diseases.*—Excellent with respect to rose Black Spot, Powdery Mildew, and Rust.

Plants of the new 'Meiglise' variety have not been observed under all possible environmental conditions to date. Accordingly, it is possible that the phenotypic expression may vary somewhat with changes in light intensity and duration, cultural practices, and other environmental conditions without variance in the genotype.

I claim:

1. A new and distinct variety of Shrub rose plant characterized by the following combination of characteristics:

(a) exhibits a spreading ground cover growth habit, (b) abundantly forms in clusters on a nearly continuous basis attractive single fragrant bright white blossoms that self clean well, (c) forms very glossy medium green foliage that contrasts well with the blossom coloration, (d) develops well following the rooting of cuttings, budding and grafting, (e) is highly resistant to Black Spot, Powdery Mildew and Rust, and (f) is particularly well suited for providing attractive ornamentation as a mass planting substantially as herein shown and described.

* * * * *

*Rosa* 'Meiglise'

0
1cm
2
3
4
5
6
7
8

Rosa 'Meiglise'

0
1cm
2
3
4
5
6
7
8

Rosa 'Meiglise'

0
1cm
2
3
4
5
6
7
8
9
10
11

Figure 1:
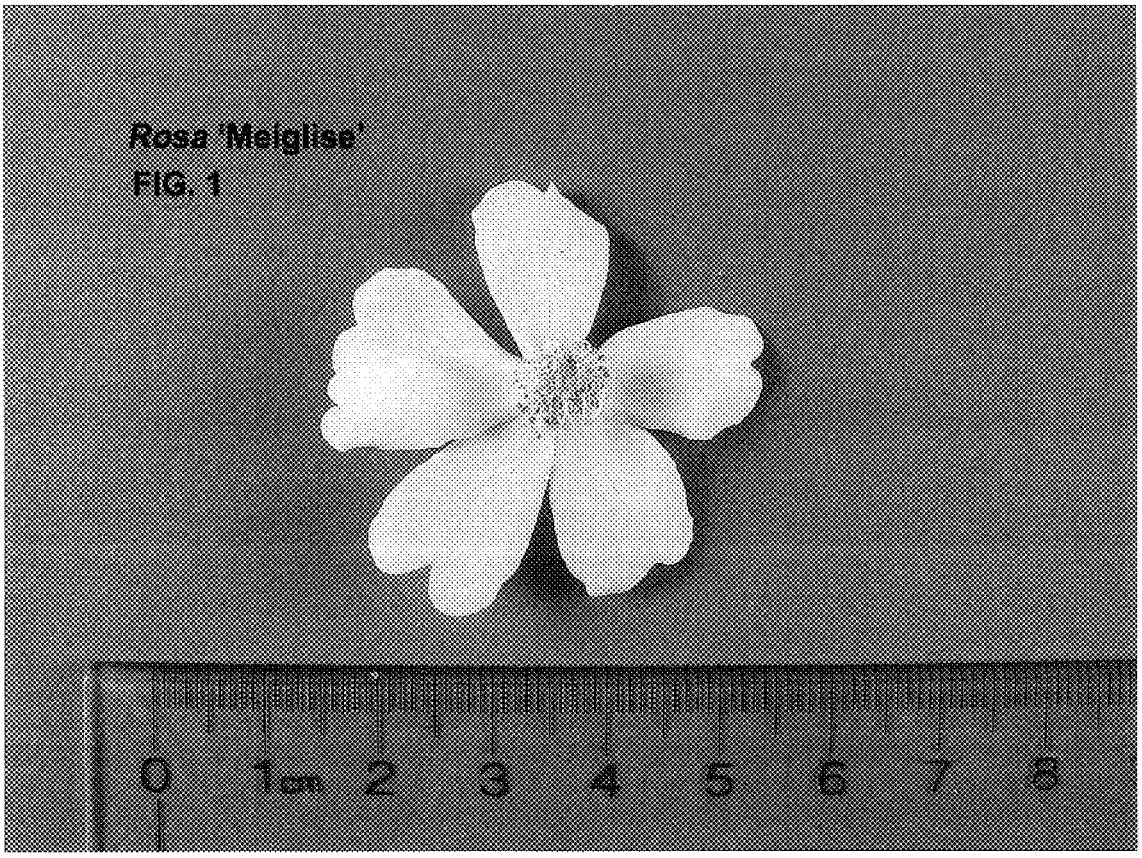
FIG. 1 illustrates a specimen of a typical open flower—plan view—obverse.
Figure 2:
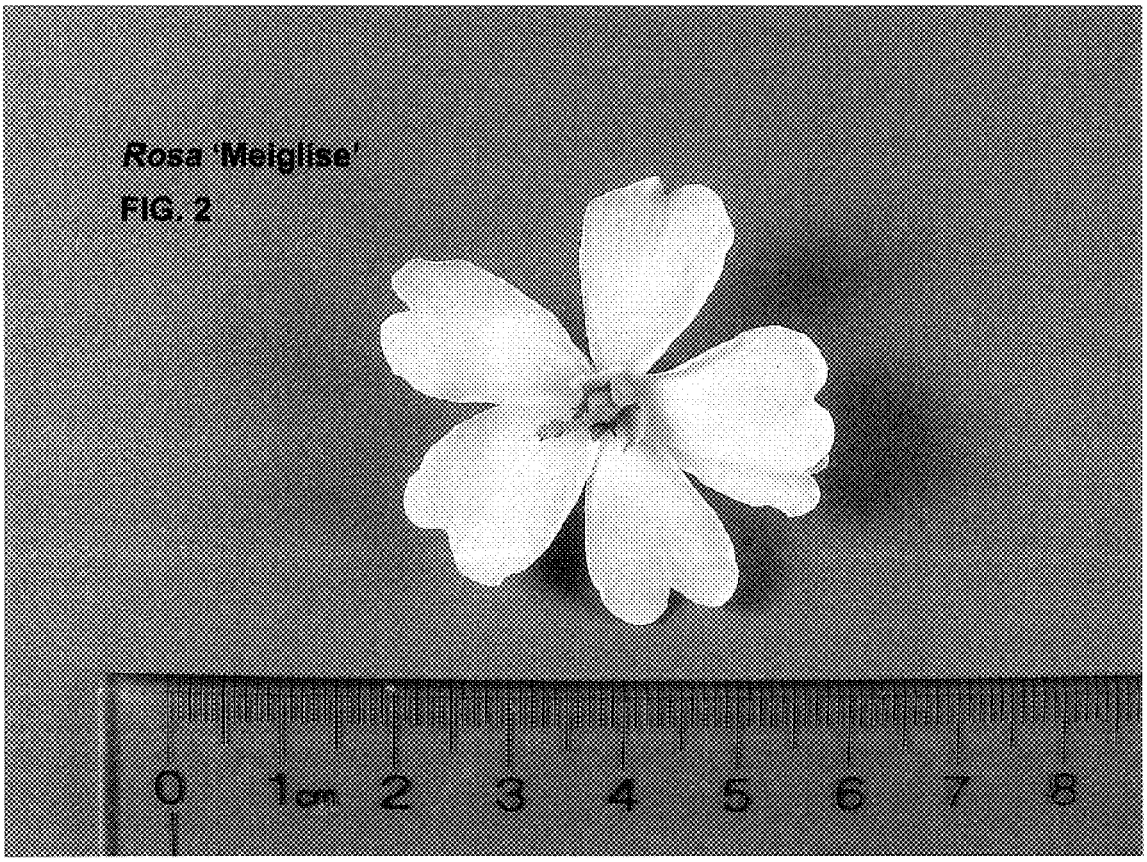
FIG. 2 illustrates a specimen of a typical open flower—plan view—reverse.
Figure 3:
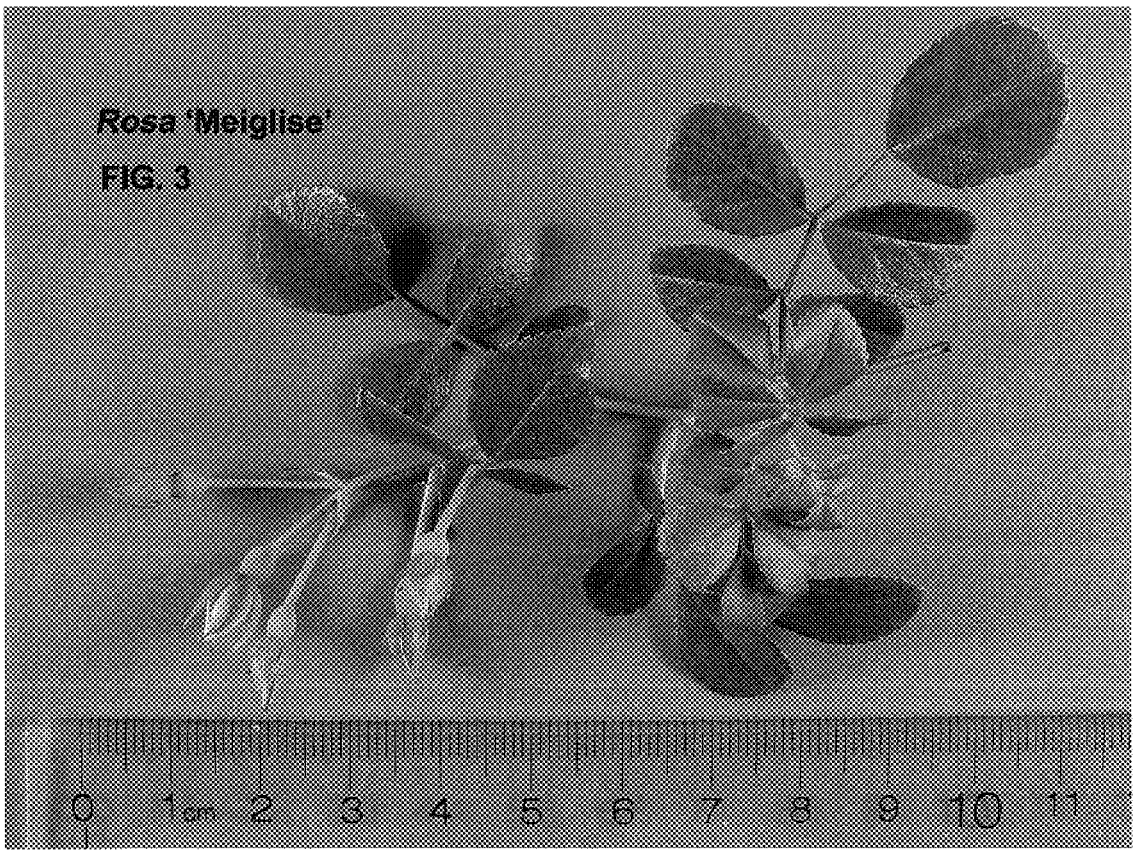
FIG. 3 illustrates a specimen of a typical branch with foliage and flower buds one of which is beginning to open.
Figure 4:
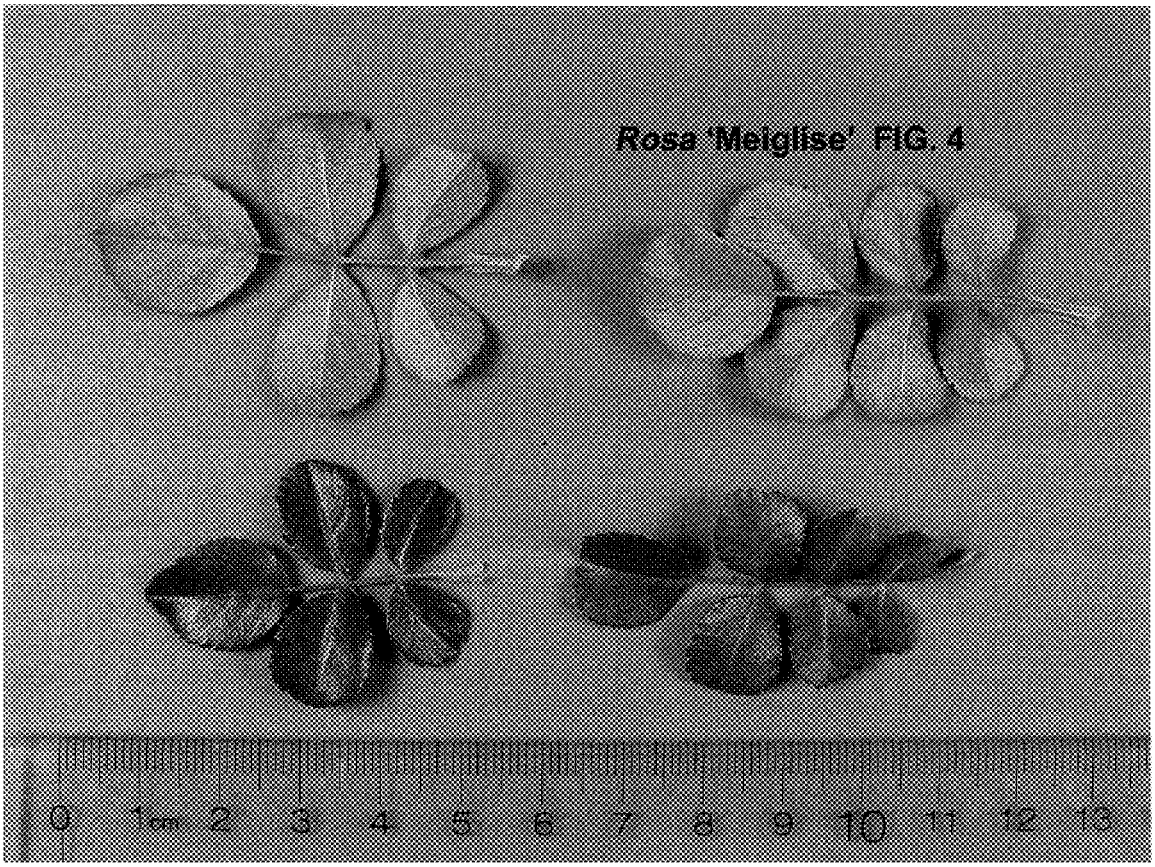
FIG. 4 illustrates specimens of typical leaves with five leaflets (left) and seven leaflets (right) with the under (at top) and upper (at bottom) surfaces being shown.

*Rosa* 'Meiglise' FIG. 4

*Rosa* 'Meiglise'